United States Patent [19]

Plummer

[11] Patent Number: 4,737,509
[45] Date of Patent: Apr. 12, 1988

[54] N-(4-(2-ARYLTETRAFLUOROETHOXY)-3-METHOXYPHENYL)-N'-BENZOYLUREA INSECT GROWTH REGULATORS

[75] Inventor: Ernest L. Plummer, Yardley, Pa.

[73] Assignee: FMC Corporation, Philadelphia, Pa.

[21] Appl. No.: 938,090

[22] Filed: Dec. 4, 1986

[51] Int. Cl.$^4$ .................... A01N 43/12; A01N 43/50; A01N 47/34; C07D 233/96
[52] U.S. Cl. .................... 514/386; 514/469; 514/594; 548/307; 549/462; 549/471; 564/44
[58] Field of Search .......... 564/44; 548/307; 514/386, 594, 469; 549/462, 471

[56] References Cited

U.S. PATENT DOCUMENTS

| | | | |
|---|---|---|---|
| 4,013,717 | 3/1977 | Wellinga et al. | 564/44 |
| 4,240,979 | 12/1980 | Baumann et al. | 564/44 |
| 4,350,706 | 9/1982 | Brouwer et al. | 564/23 X |
| 4,468,405 | 8/1984 | Rigertink et al. | 548/307 X |
| 4,567,295 | 1/1986 | Brouwer et al. | 564/44 |

FOREIGN PATENT DOCUMENTS

| | | | |
|---|---|---|---|
| 767161 | 11/1971 | Belgium | 564/44 |
| 23884 | 2/1981 | European Pat. Off. | 564/44 |

*Primary Examiner*—Richard A. Schwartz
*Attorney, Agent, or Firm*—William Schmonsees; H. Robinson Ertelt

[57] ABSTRACT

Compounds of the formula

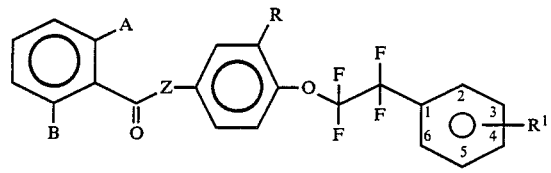

wherein Z is

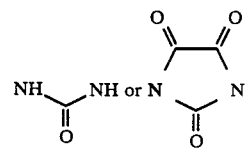

compositions containing the compounds, and their utility as dietary and foliar insecticides are disclosed and exemplified.

18 Claims, No Drawings

N-(4-(2-ARYLTETRAFLUOROETHOXY)-3-METHOXYPHENYL)-N'-BENZOYLUREA INSECT GROWTH REGULATORS

BACKGROUND OF THE INVENTION

The present invention pertains to novel pesticidal [(substituted phenyl)tetrafluoroethoxy]phenylbenzoylureas. In particular, it pertains to N-[[[4-[2-(substituted phenyl)-1,1,2,2-tetrafluoroethoxy]phenyl]amino]carbonyl]benzamides which disrupt the normal developmental sequence of insects.

Other benzoylurea insect growth regulators are described in commonly assigned U.S. Ser. No. 816,661, filed Jan. 7, 1986, U.S. Ser. No. 838,215 filed Mar. 10, 1986, and U.S. Ser. No. 867,888, filed May 19, 1986.

DESCRIPTION OF RELATED ART

U.S. Pat. No. 4,013,717 discloses insecticidal activity for certain N-phenyl benzamides having halogen, alkyl, haloalkyl, alkoxy, phenyl, and phenoxy substituted on the N-phenyl.

U.S. Pat. No. 4,350,706 also discloses substituted N-phenyl benzamides with a variety of substituents for N-phenyl.

Neither reference discloses nor recognizes the particular utility of phenyl tetrafluoroethoxy-substituents on N-phenyl in benzoylurea insect growth regulators.

SUMMARY OF THE INVENTION

The compounds of this invention are highly active insecticides which act by interfering with the normal molting process of insect larvae, similar to the insecticidal action of diflubenzuron.

Novel compounds such as N-[[[4-[2-(4-chlorophenyl)-1,1,2,2-tetrafluoroethoxy]-3-methoxyphenyl]amino]carbonyl]-2,6-difluorobenzamide and 1-[(2,6-difluorophenyl)carbonyl]-3-[4-(1,1,2,2-tetrafluoro-2-phenylethoxy)-3-methoxyphenyl]imidazolidinetrione have controlled southern armyworm and cabbage looper at rates as low as 2.0 to 3.0 ppm in foliar testing.

The compounds of the present invention are represented by the following formulae:

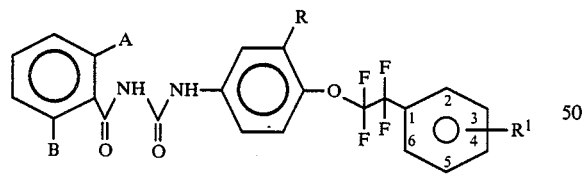

or

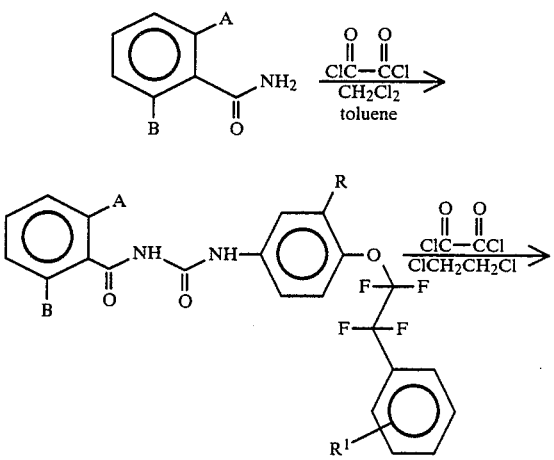

wherein A and B are independently hydrogen or halogen; R is hydrogen, halogen, or alkoxy; and $R^1$ is hydrogen, halogen, alkyl, alkoxy, benzyloxy, substituted amino, or may be a cyclic group joined at the 3- and 4-position (e.g., 3-$CF_2CF_2O$-4).

The terms "alkyl" and "alkoxy" include stright or branched chain compounds having from 1 to 6 carbon atoms.

The cyclic group is a 5 to 7 membered ring, including the atoms at positions 3 and 4 of the phenyl. The cyclic group optionally contains 1 or 2 heteroatoms or substituted atoms.

DETAILED DESCRIPTION OF THE INVENTION

The compounds of this invention were prepared by following the general methods disclosed in Wellinga, J. Arg. Food Chem., 21 (3), 348, 1973 and U.S. Pat. No. 4,013,717.

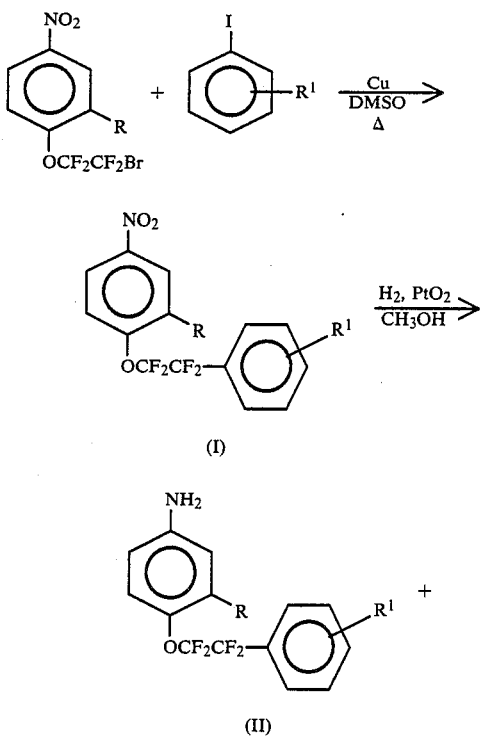

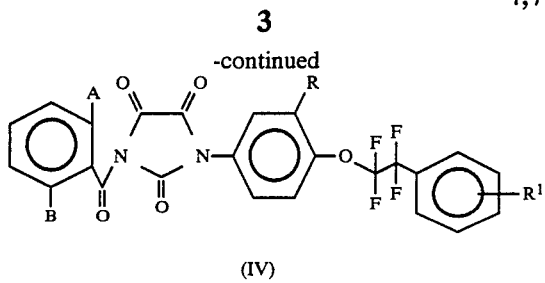

(IV)

Reaction of a substituted-4-(2-bromo-1,1,2,2-tetrafluoroethoxy)nitrobenzene with an appropriately substituted iodobenzene and copper powder in dimethyl sulfoxide produced the 3-sustituted-4-[(1,1,2,2-tetrafluoro-2-substituted phenyl)ethoxy]nitrobenzene (I). Hydrogenation of (I) produced the corresponding aniline (II). Reaction of a halogenzamide first with oxalyl chloride in methylene chloride and toluene followed by aniline (II) produced the N-[[[4-[2-(substituted phenyl)]-1,1,2,2-tetrafluoroethoxy]phenyl]amino]carbonyl]benzamide (III). Further treatment of (III) with oxalyl chloride and 1,2-dichloroethane produced the corresponding imidazolidinetrione (IV).

EXAMPLE 1

N-[[[4-[2-(4-Chlorophenyl)-1,1,2,2-Tetrafluoroethoxy]-3-Methoxyphenyl]Amino]Carbonyl]-2,6-Difluorobenzamide Step A: 4-[2-(4-Chlorophenyl)-1,1,2,2-tetrafluoroethoxy]-3-methoxynitrobenzene Under a dry argon atmosphere a stirred mixture of 4-(2-bromo-1,1,2,2-tetrafluoroethoxy)-3-methoxynitrobenzene (5.0 g, 0.014 mole), 4-chloroiodobenzene (3.4 g, 0.014 mole), and copper powder (4.6 g, 0.072 mole, 200 mesh) in dimethyl sulfoxide (75 mL) was heated at about 160° C. for approximately three hours. The reaction mixture was allowed to cool to room temperature and stirred for an additional 18 hours. The cool mixture was poured into 200 mL of 2N hydrochloric acid, the resultant mixture was extracted with three 100 mL portions of methylene chloride. The extracts were combined and washed in succession with 2N hydrochloric acid, an aqueous, saturated, sodium chloride solution, and 2N aqueous sodium hydroxide. The washed organic phase was dried over anhydrous magnesium sulfate and filtered. The filtrate was evaporated under reduced pressure leaving an oil. This oil was purified by column chromatography on silica gel, eluting with n-heptane:toluene (90:10), to yield 1.4 g of 4-[2-(4-chlorophenyl)-1,1,2,2-tetrafluoroethoxy]-3-methoxynitrobenzene as an oil.

The nmr and ir spectra were consistent with the proposed structure.

Step B: 4-[2-(4-chlorophenyl)-1,1,2,2-tetrafluoroethoxy]-3-methoxyaniline

Hydrogenation of 4-[2-(4-chlorophenyl)-1,1,2,2-tetrafluoroethoxy]-3-methoxynitrobenzene (0.90 g, 0.0024 mole) with a catalytic amount of platinum oxide (0.25 g) in methanol (150 mL) produced 0.84 g of 4-[2-(4-chlorophenyl)-1,1,2,2-tetrafluoroethoxy]-3-methoxyaniline.

The ir spectrum was consistent with the proposed structure.

Step C: N-[[[4-[2-(4-chlorophenyl)-1,1,2,2-tetrafluoroethoxy)-3-methoxyphenyl]amino]carbonyl]-2,6-difluorobenzamide A stirred mixture of 2,6-difluorobenzamide (0.37 g, 0.027 mole), oxalyl chloride (0.33 g, 0.0026 mole) and methylene chloride (3.0 mL) in toluene (80 mL) was heated at reflux for three hours. Approximately 40 mL of solvent was removed by distillation under reduced pressure. A solution of 4-[2-(4-chlorophenyl)-1,1,2,2-tetrafluoroethoxy]-3-methoxyaniline (0.83 g, 0.0024 mole) in toluene (40 mL) was added to the reaction mixture. The resultant solution was stirred at room temperature for approximately 18 hours. About 40 mL of the solvent was removed by evaporation under reduced pressure, leaving a liquid residue. Approximately 100 mL of n-heptane was added to the residue, and the mixture was stirred at room temperature, slowly forming a precipitate. This solid was collected by filtration to yield 1.2 g of N-[[[4-[2-(4-chlorophenyl)-1,1,2,2-tetrafluoroethoxy]-3-methoxyphenyl]amino]carbonyl]-2,6-difluorobenzamide, m.p. 133°–134.5° C., Compound 10 of Table 1.

The nmr and ir spectra were consistent with the proposed structure.

Analysis calc'd for $C_{23}H_{15}ClF_6N_2O_4$: C 51.85; H 2.83; Found: C 52.11; H 2.88.

EXAMPLE 2

1-[(2,6-Difluorophenyl)Carbonyl)-3-[4-(1,1,2,2-Tetrafluoro-2-Phenylethoxy)-3-Methoxyphenyl-]Imidazolidinetrione Under a dry argon atmosphere, oxalyl chloride (0.11 g, 0.00090 mole) was added to a stirred solution of N-[[[4-(1,1,2,2-tetrafluoro-2-phenylethoxy)-3-methoxyphenyl]amino]carbonyl]-2,6-difluorobenzamide (0.45 g, 0.00090 mole, Compound 3—prepared by the method of Example 1 using iodobenzene) in 1,2-dichloroethane (10 mL). This mixture was stirred at room temperature for two days and then was heated at reflux for six hours. The mixture was allowed to cool to room temperature and stirred for an additional 18 hours. The solvent was removed under reduced pressure leaving an oily residue. This oil was purified by column chromatography on silica gel, eluting with methylene chloride, to yield 0.38 g of 1-[(b 2,6-difluorophenyl)carbonyl]-3-[4-(1,1,2,2-tetrafluoro-2-phenylethoxy)-3-methoxyphenyl-]imidazolidinetrione as an oil, Compound 22 of Table 1.

The nmr and ir spectra were consistent with the proposed structure.

Analysis calc'd for $C_{25}H_{14}F_6N_2O_6$: C 54.36; H 2.55; Found: C 53.64; H 2.62.

Table 1 lists the compounds prepared and Table 2 contains characterizing data for the compounds.

The compounds of this invention were tested by incorporating the compounds into the diet of the test insects, second instar southern armyworm (*Spodoptera eridania*) and cabbage looper (*Trichoplusia ni*). The tests were conducted in duplicate at a rate of 200 ppm, using ten larvae per replicate. Each test was read one day, three to five days, and six to eleven days after infestation to determine the number dead after at least one molt.

The test media consisted of a clay formulation (dust) of the test compound mixed with the insect diet. The components of the test media and its method of preparation are:

Composition of Insect Diet

| | Parts by Weight |
|---|---|
| Pinto beans | 12.90 |
| Wheat germ | 5.68 |

| | Parts by Weight |
|---|---|
| Brewer's dried yeast | 3.64 |
| Ascorbic acid | 0.37 |
| Methyl paraben | 0.23 |
| Sorbic acid | 0.11 |
| Sodium benzoate | 0.00284 |
| Agar | 0.71 |
| Formalin (40%) | 0.23 |
| Water | 76.13 |

The agar was dissolved with heating in one-half the water and was brought to a boil. Simultaneously, all other ingredients except the formalin were placed in a blender with the remaining water and were reduced to a smooth, homogenous mixture. This mixture was added to the boiling agar. Immediately, the formalin was added with mixing.

The compounds of this invention were formulated as a dust on a clay base. The dust consisted of the following:

| Clay Formulation | 5% Dust |
|---|---|
| Test compound | 5.00 |
| Base | 95.00 |
| 96% Attaclay | |
| 2% highly purified sodium lignosulfonate (100%) | |
| 2% powdered sodium alkylnaphthalene sulfonate (75%) | |
| | 100.00 |

These formulations were prepared by mixing the active ingredient (i.e. the test compound) with the dry base.

Test media containing 200 ppm of the test compound were prepared by making a 'stock solution' from 1000 mg of a 5% dust formulation stirred well with 5 mL of distilled water in a vial. One milliliter of the 'stock solution' was added to 50 mL of warm, i.e. molten, insect diet in a plastic petri dish which was then mixed thoroughly. After cooling to room temperature, the gelled test media were infested with test larvae and covered.

The results of diet incorporated testing are summarized in Table 3.

Some compounds of this invention were also tested in foliar evaluations against southern armyworm, cabbage looper, and Mexican bean beetle (*Epilachna varivestis*), according to the following procedure:

A test solution containing 500 ppm of the test compound was prepared by making a 'stock solution' from 250 mg of a 5% dust formulation, one drop of cotton seed oil, and one drop of octylphenoxypolyethoxyethanol in 25 mL of distilled water. A 64 ppm test solution was prepared by dilution of 5 mL of stock solution with 39 mL of water, containing 10 drops each of cotton seed oil and octylphenoxypolyethoxyethanol per liter.

The test solution was sprayed on pinto bean plants to run-off. After the plants were dry, they were cut at the base of the stem. The stem of each plant was inserted into a hole made in the bottom of a wax coated paper cup, one plant per cup. Each plant was infested with ten first instar southern armyworm or cabbage looper larvae to ensure that a molt would occur prior to reading the test. Cheese cloth was placed over the top of each cup and held in place by a lid with a 1" to 2.5" diameter hole. The cups containing the tests were placed in a rack which submerges the stem of each plant in a tray of distilled water. The tests were kept in a growth chamber at constant humidity (50%) and temperature (25° C.) for four days, at which time the tests were read. The tests were run in duplicate. The results of these tests are summarized in Table 4.

In the normal use of the insecticidal benzoylureas of the present invention, the benzoylureas usually will not be employed free from admixture or dilution, but ordinarily will be used in a suitable formulation composition compatible with the method of application and comprising an insecticidally effective amount of benzoylurea. The benzoylureas of this invention, like most pesticidal agents, may be blended with the agriculturally acceptable surface-active agents and carriers normally employed for facilitting the dispersion of active ingredients, recognizing the accepted fact that the formulation and mode of application of an insecticide may affect the activity of the material. The present benzoylureas may be applied, for example, as sprays, dusts, or granules to the area where pest control is desired, the type of application varying of course with the pest and the environment. Thus, the benzoylureas of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the benzoylureas. The granule particles are relatively large, a diameter of about 400–2500 microns typically. The particles are either impregnated with the benzoylurea from solution or coated with the benzoylurea, adhesive sometimes being employed. Granules generally contain 0.05–10%, preferably 0.5–5%, active ingredient as the insecticidally effective amount.

Dusts are admixtures of the benzoylureas with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of benzoylurea, such as N-[[[4-[2-(4-chlorophenyl)-1,1,2,2-tetrafluoroethoxy)-3-methoxyphenyl]amino]carbonyl]-2,6-difluorobenzamide, and 99 parts of talc.

The benzoylureas of the present invention may be made into liquid concentrates by dissolution or emulsification in suitable liquids and into solid concentrations by admixture with talc, clays, and other known solid carriers used in the pesticide art. The concentrates are compositions containing, as an insecticidally effective amount, about 5–50% benzoylurea, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium lauryl sulfate as wetting agents, 25 parts of N-[[[4-[2-(3-chlorophenyl)-1,1,2,2- tetrafluoroethoxy)-3-methoxyphenyl]amino]carbonyl]-2,6-difluorobenzamide, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the benzoylurea with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfates of higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

An insecticidally effective amount of benzoylurea in an insecticidal composition diluted for application is normally in the range of about 0.001% to about 8% by weight. Many variations of spraying and dusting compositions known in the art may be used by substituting the benzoylureas of this invention into compositions known or apparent in the art.

The insecticidal compositions of this invention may be formulated with other active ingredients, including other insecticides, nematicides, acaricides, fungicides, plant growth regulators, fertilizers, etc. In using the compositions to control insects, it is only necessary that an insecticidally effective amount of benzoylurea be applied to the locus where control is desired. Such locus may, e.g., be the insects themselves, plants upon which the insects feed, or the insect habitat. When the locus is soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

TABLE 1
COMPOUNDS PREPARED

| Cmpd No. | A | B | R | $R^1$ |
|---|---|---|---|---|
| 1 | F | F | H | H |
| 2 | F | F | Cl | H |
| 3 | F | F | $OCH_3$ | H |
| 4 | Cl | H | $OCH_3$ | 3-Cl |
| 5 | F | F | $OCH_3$ | 2-F |
| 6 | F | F | $OCH_3$ | 3-F |
| 7 | F | F | $OCH_3$ | 4-F |
| 8 | F | F | $OCH_3$ | 2-Cl |
| 9 | F | F | $OCH_3$ | 3-Cl |
| 10 | F | F | $OCH_3$ | 4-Cl |
| 11 | Cl | H | $OCH_3$ | 2-$CH_3$ |
| 12 | Cl | H | $OCH_3$ | 3-$CH_3$ |
| 13 | Cl | H | $OCH_3$ | 4-$CH_3$ |
| 14 | F | F | $OCH_3$ | 2-$CH_3$ |
| 15 | F | F | $OCH_3$ | 3-$CH_3$ |
| 16 | F | F | $OCH_3$ | 4-$CH_3$ |
| 17 | F | F | $OCH_3$ | 4-CO-phenyl |
| 18 | F | F | $OCH_3$ | 4-$OCH(CH_3)_2$ |
| 19 | F | F | $OCH_3$ | 4-$O(CH_2)_4CH_3$ |
| 20 | F | F | $OCH_3$ | 4-$N(CH_3)_2$ |
| 21 | F | F | $OCH_3$ | 3-$CF_2CF_2O$—4 |
| 22 | F | F | $OCH_3$ | H |
| 23 | Cl | H | $OCH_3$ | 3-$CH_3$ |
| 24 | F | F | $OCH_3$ | 3-$CH_3$ |

TABLE 2
IDENTIFYING PROPERTIES OF THE COMPOUNDS

| Cmpd No. | Melting Point (°C.) | Empirical Formula | Elemental Analysis | | |
|---|---|---|---|---|---|
| | | | | C | H |
| 1 | 174–175.5 | $C_{22}H_{14}F_6N_2O_3$ | C | 56.42 | 3.01 |
| | | | F | 55.35 | 2.87 |
| 2 | 157.5–158.5 | $C_{22}H_{13}ClF_6N_2O_3$ | C | 52.56 | 2.60 |
| | | | F | 52.88 | 2.83 |
| 3 | 104.5–105.5 | $C_{23}H_{16}F_6N_2O_4$ | C | 55.43 | 3.23 |
| | | | F | 56.17 | 3.56 |
| 4 | 143.5–145 | $C_{23}H_{16}Cl_2F_4N_2O_4$ | C | 52.00 | 3.03 |
| | | | F | 51.90 | 3.15 |
| 5 | 137–138 | $C_{23}H_{15}F_7N_2O_4$ | C | 53.50 | 2.93 |
| | | | F | 53.70 | 2.67 |
| 6 | 130–131 | $C_{23}H_{15}F_7N_2O_4$ | C | 53.50 | 2.93 |
| | | | F | 53.58 | 3.18 |
| 7 | 117–118 | $C_{23}H_{15}F_7N_2O_4$ | C | 53.50 | 2.93 |
| | | | F | 53.29 | 2.87 |
| 8 | 129.5–131 | $C_{23}H_{15}ClF_6N_2O_4$ | C | 51.85 | 2.83 |
| | | | F | 52.03 | 2.88 |
| 9 | 139–140.5 | $C_{23}H_{15}ClF_6N_2O_4$ | C | 51.85 | 2.83 |
| | | | F | 50.94 | 2.79 |
| 10 | 133–134.5 | $C_{23}H_{15}ClF_6N_2O_4$ | C | 51.85 | 2.83 |
| | | | F | 52.11 | 2.88 |
| 11 | 141–142 | $C_{24}H_{19}ClF_4N_2O_4$ | C | 56.43 | 3.75 |
| | | | F | 56.10 | 3.48 |

TABLE 2-continued

IDENTIFYING PROPERTIES OF THE COMPOUNDS

| Cmpd No. | Melting Point (°C.) | Empirical Formula | | Elemental Analysis | |
|---|---|---|---|---|---|
| | | | | C | H |
| 12 | 149-150 | $C_{24}H_{19}ClF_4N_2O_4$ | C | 56.43 | 3.75 |
| | | | F | 56.18 | 3.47 |
| 13 | 107-108.5 | $C_{24}H_{19}ClF_4N_2O_4$ | C | 56.43 | 3.75 |
| | | | F | 56.35 | 3.50 |
| 14 | 105-106.5 | $C_{24}H_{18}F_6N_2O_4$ | C | 56.26 | 3.54 |
| | | | F | 56.09 | 3.80 |
| 15 | 112-113.5 | $C_{24}H_{18}F_6N_2O_4$ | C | 56.26 | 3.54 |
| | | | F | 55.86 | 3.15 |
| 16 | 137-138.5 | $C_{24}H_{18}F_6N_2O_4$ | C | 56.26 | 3.54 |
| | | | F | 55.29 | 2.94 |
| 17 | 135-140 | $C_{30}H_{20}F_6N_2O_5$ | C | 59.80 | 3.35 |
| | | | F | 60.49 | 3.85 |
| 18 | 128-131 | $C_{26}H_{22}F_6N_2O_5$ | | | |
| 19 | 104-106 | $C_{28}H_{26}F_5N_2O_5$ | | | |
| 20 | 140-145 | $C_{25}H_{21}F_6N_3O_4$ | C | 55.45 | 3.91 |
| | | | F | 55.25 | 3.65 |
| 21 | 140-141 | $C_{25}H_{14}F_{10}N_2O_5$ | C | 49.03 | 2.30 |
| | | | F | 49.05 | 2.60 |
| 22 | oil | $C_{25}H_{14}F_6N_2O_6$ | C | 54.36 | 2.55 |
| | | | F | 53.64 | 2.67 |
| 23 | 125.5-127 | $C_{26}H_{17}ClF_4N_2O_6$ | C | 57.74 | 3.16 |
| | | | F | 55.47 | 3.70 |
| 24 | oil | $C_{26}H_{16}F_6N_2O_6$ | C | 57.58 | 2.97 |
| | | | F | 57.48 | 3.34 |

TABLE 3

RESULTS OF DIET INCORPORATED SCREENING TESTS
% Kill at 200 ppm
(5% Formulation on Clay)

| Cmpd No. | Exposure Period (Days) | Insects Tested | |
|---|---|---|---|
| | | Southern Armyworm | Cabbage Looper |
| 1 | 1 | 0 | 40 |
| | 4 | 100 | 90 |
| | 8 | 100 | 100 |
| 2 | 1 | 0 | 10 |
| | 4 | 100 | 100 |
| | 8 | 100 | 100 |
| 3 | 1 | 0 | 0 |
| | 6 | 100 | 100 |
| | 8 | 100 | 100 |
| 4 | 2 | 0 | 10 |
| | 8 | 100 | 100 |
| 5 | 1 | 0 | 90 |
| | 3 | 50 | 100 |
| | 8 | 100 | 100 |
| 6 | 1 | 0 | 60 |
| | 3 | 50 | 80 |
| | 8 | 100 | 100 |
| 7 | 1 | 40 | 80 |
| | 3 | 100 | 90 |
| | 8 | 100 | 100 |
| 8 | 2 | 0 | 70 |
| | 8 | 100 | 100 |
| 9 | 2 | 0 | 30 |
| | 8 | 100 | 100 |
| 10 | 2 | 0 | 80 |
| | 8 | 100 | 100 |
| 11 | 1 | 0 | 80 |
| | 4 | 0 | 100 |
| | 8 | 90 | 100 |
| 12 | 1 | 0 | 10 |
| | 4 | 60 | 100 |
| | 8 | 100 | 100 |
| 13 | 1 | 0 | 20 |
| | 4 | 100 | 100 |
| | 8 | 100 | 100 |
| 14 | 1 | 0 | 30 |
| | 4 | 70 | 100 |
| | 8 | 100 | 100 |
| 15 | 1 | 0 | 0 |
| | 4 | 70 | 100 |
| | 8 | 100 | 100 |
| 16 | 1 | 0 | 0 |
| | 4 | 60 | 100 |

TABLE 3-continued

RESULTS OF DIET INCORPORATED SCREENING TESTS
% Kill at 200 ppm
(5% Formulation on Clay)

| Cmpd No. | Exposure Period (Days) | Insects Tested | |
|---|---|---|---|
| | | Southern Armyworm | Cabbage Looper |
| | 8 | 100 | 100 |
| 17 | 1 | 0 | 0 |
| | 5 | 60 | 50 |
| | 8 | 60 | 70 |
| 18 | 1 | 0 | 0 |
| | 4 | 100 | 100 |
| | 8 | 100 | 100 |
| 19 | 1 | 0 | 10 |
| | 4 | 100 | 100 |
| | 8 | 100 | 100 |
| 20 | 2 | 0 | 20 |
| | 5 | 80 | 100 |
| | 8 | 90 | 100 |
| 21 | 1 | 0 | 0 |
| | 4 | 90 | 100 |
| | 8 | 100 | 100 |
| 22 | 3 | 0 | 30 |
| | 7 | 40 | 80 |
| 23 | 6 | 90 | 100 |
| | 7 | 90 | 100 |
| 24 | 6 | 70 | 90 |
| | 7 | 100 | 100 |

TABLE 4

RESULTS OF FOLIAR EVALUATIONS

| | % Kill | | |
|---|---|---|---|
| Cmpd No. | Cabbage Looper[1] | Southern Armyworm[1] | Mexican Bean Beetle[2] |
| 2 | 80 | 95 | — |
| 3 | 95 | 45 | — |
| 4 | 100 | 100 | 70 |
| 5 | 100 | 100 | 40 |
| 6 | 100 | 100 | 45 |
| 7 | 100 | 100 | 50 |
| 8 | 100 | 100 | 75 |
| 9 | 100 | 100 | 80 |
| 10 | 100 | 100 | 95 |
| 12 | 15 | 0 | 20 |
| 14 | 65 | 90 | 80 |
| 15 | 35 | 20 | 90 |
| 16 | 20 | 85 | 60 |
| 21 | 100 | — | 85 |
| 22 | 100 | 100 | — |

[1]Tested at 64 ppm
[2]Tested at 500 ppm

I claim:
1. A compound of the formula

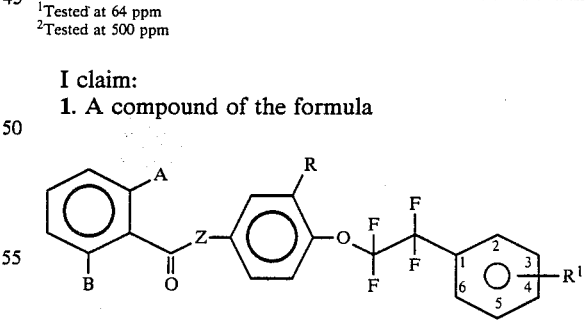

wherein Z is

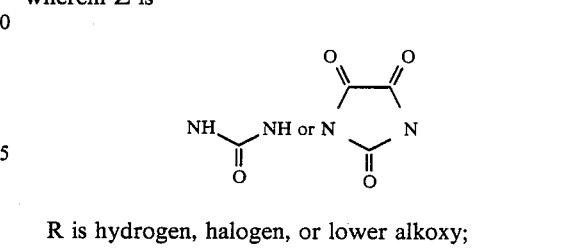

R is hydrogen, halogen, or lower alkoxy;

$R^1$ is hydrogen, halogen, lower alkyl, lower alkoxy, benzyloxy, lower alkyl substituted amino, or $R^1$ completes a benzofuranyl ring, optionally substituted with halogen atoms; and A and B are independently hydrogen or halogen.

2. A compound of claim 1 in which R is lower alkoxy.

3. A compound of claim 2 in which R is methoxy.

4. A compound of claim 1 in which $R^1$ is a halogen.

5. A compound of claim 4 in which $R^1$ is fluorine or chlorine.

6. A compound of claim 1 in which R is lower alkoxy and $R^1$ is a halogen.

7. A compound of claim 1 in which R is methoxy and $R^1$ is fluorine or chlorine.

8. The compound of claim 1 which is N-[[[4-[2-(3-chlorophenyl)-1,1,2,2-tetrafluoroethoxy]-3-methoxyphenyl]amino]carbonyl]-2-chlorobenzamide.

9. The compound of claim 1 which is N-[[[4-[2-(2-fluorophenyl)-1,1,2,2-tetrafluoroethoxy]-3-methoxyphenyl]amino]carbonyl]-2,6-difluorobenzamide.

10. The compound of claim 1 which is N-[[[4-[2-(3-fluorophenyl)-1,1,2,2-tetrafluoroethoxy]-3-methoxyphenyl]amino]carbonyl]-2,6-difluorobenzamide.

11. The compound of claim 1 which is N-[[[4-[2-(4-fluorophenyl)-1,1,2,2-tetrafluoroethoxy]-3-methoxyphenyl]amino]carbonyl]-2,6-difluorobenzamide.

12. The compound of claim 1 which is N-[[[4-[2-(2-chlorophenyl)-1,1,2,2-tetrafluoroethoxy]-3-methoxyphenyl]amino]carbonyl]-2,6-difluorobenzamide.

13. The compound of claim 1 which is N-[[[4-[2-(3-chlorophenyl)-1,1,2,2-tetrafluoroethoxy]-3-methoxyphenyl]amino]carbonyl]-2,6-difluorobenzamide.

14. The compound of claim 1 which is N-[[[4-[2-(4-chlorophenyl)-1,1,2,2-tetrafluoroethoxy)-3-methoxyphenyl]amino]carbonyl]-2,6-difluorobenzamide.

15. The compound of claim 1 which is N-[[[4-[2-(2,3-dihydro-2,2,3,3-tetrafluorobenzofuran-5-yl)-1,1,2,2-tetrafluoroethoxy]-3-methoxyphenyl]amino]carbonyl]-2,6-difluorobenzamide.

16. The compound of claim 1 which is 1-[(2,6-difluorophenyl)carbonyl]-3-[4-(1,1,2,2-tetrafluoro-2-phenylethoxy)-3-methoxyphenyl]imidazolidinetrione.

17. An insecticidal composition comprising an insecticidally effective amount of a compound of claim 1 in admixture with at least one suitable carrier, solvent, adjuvant, or complementary pesticide.

18. A method for controlling insects by applying to the locus where control is desired an insecticidally effective amount of a compound of claim 1.

* * * * *